(12) United States Patent
Kuhn et al.

(10) Patent No.: US 8,795,226 B2
(45) Date of Patent: Aug. 5, 2014

(54) CANNULA ASSEMBLY FOR CO-DELIVERY OF MEDICAMENTS

(75) Inventors: Bernd Kuhn, Frankfurt am Main (DE);
Gerrit Hauck, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 155 days.

(21) Appl. No.: 13/379,592

(22) PCT Filed: Jun. 24, 2010

(86) PCT No.: PCT/EP2010/058984
§ 371 (c)(1),
(2), (4) Date: Apr. 15, 2012

(87) PCT Pub. No.: WO2010/149734
PCT Pub. Date: Dec. 29, 2010

(65) Prior Publication Data
US 2012/0197210 A1 Aug. 2, 2012

Related U.S. Application Data

(60) Provisional application No. 61/220,438, filed on Jun. 25, 2009.

(30) Foreign Application Priority Data

Aug. 11, 2009 (EP) .................................. 09010325

(51) Int. Cl.
*A61M 37/00* (2006.01)
*A61M 5/00* (2006.01)
*A61M 5/31* (2006.01)

(52) U.S. Cl.
USPC .................. 604/87; 604/85; 604/89; 604/240

(58) Field of Classification Search
USPC ....................... 604/82–89, 416, 200, 240–241
See application file for complete search history.

(56) References Cited

U.S. PATENT DOCUMENTS

| | | | |
|---|---|---|---|
| 4,197,846 A * | 4/1980 | Bucalo | 604/506 |
| 5,330,426 A | 7/1994 | Kriesel et al. | |
| 5,395,319 A * | 3/1995 | Hirsch et al. | 604/60 |
| 6,562,002 B1 | 5/2003 | Taylor | |
| 2002/0188196 A1 | 12/2002 | Burbank et al. | |
| 2005/0070959 A1 | 3/2005 | Cichocki, Jr. | |
| 2007/0073248 A1 | 3/2007 | Moenning | |

FOREIGN PATENT DOCUMENTS

| | | |
|---|---|---|
| FR | 2210910 | 7/1974 |
| FR | 2775436 A1 | 9/1999 |
| WO | 03009890 A2 | 2/2003 |

* cited by examiner

*Primary Examiner* — Rebecca E Eisenberg
(74) *Attorney, Agent, or Firm* — McDonnell Boehnen Hulbert & Berghoff LLP

(57) ABSTRACT

A cannula assembly (10) comprising a hub (76) and a cannula (12) mounted in the hub (76). The cannula defines an inner space (36). The cannula comprises a distal end (16) and a proximal end (18). A first medicament (40) is provided in the inner space of the cannula. In one arrangement, the hub of the cannula assembly is configured to be coupled to an injection device (26). The cannula assembly may be removably or permanently coupled to the injection device containing a second medicament (17).

13 Claims, 4 Drawing Sheets

CANNULA ASSEMBLY FOR CO-DELIVERY OF MEDICAMENTS

CROSS REFERENCE TO RELATED APPLICATIONS

The present application is a 35 U.S.C. 371 National Application of PCT/EP2010/058984 filed Jun. 24, 2010, which claims priority to U.S. Provisional Patent Application No. 61/220,438 filed Jun. 25, 2009 and European Patent Application No. 09010325.0 filed Aug. 11, 2009, and, the entire contents of which are incorporated entirely herein by reference.

FIELD OF THE PATENT APPLICATION

The present patent application generally describes an apparatus and/or method of delivering multiple medicaments (i.e., at least two medicaments). Preferably, such medicaments are stored or housed in a first container containing a medicament such as a cartridge or ampoule that is separate from a second container or reservoir containing a further medicament. In one arrangement, these multiple medicaments are injected by way of a single injection. Preferably, one medicament is provided within a cannula assembly that is attached to a dose injection device, preferably a multiple dose injection device. Such an injection device may be either a disposable or a reusable injection device, such as a pen type injection device comprising a cartridge or ampoule containing a medicament.

BACKGROUND

There exists a general need to inject two or more medicaments simultaneously. Examples of medicaments are medicaments containing insulin, an insulin analog or an insulin derivative, GLP-1 or a GLP-1 analog, an analgesics, a hormone, a beta agonist or a corticosteroid or a combination of any of the above-mentioned active pharmaceutical ingredient per se (API) or in a dry, solid or liquid formulation further comprising one or more suitable excipients. Suitable excipients for this purpose are e.g. water, glycerol, polyols (mannitol, xylitol), macrogol or mono-, di-, oligo- or polysaccharides (e.g glucose, fructose, saccharose, dextrates, dextran 40).

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

As just one example, certain disease states require treatment using one or more different medicaments. For example, in some cases it might be beneficial to treat a certain diabetic with a long acting insulin along with a glucagon-like peptide-1 (GLP-1) or a GLP-1 analog, which is derived from the transcription product of the proglucagon gene. GLP-1 is found in the body and is secreted by the intestinal L cell as a gut hormone. GLP-1 and GLP-1 analogs possess several physiological properties that make it (and its analogs) a subject of keen investigation as a potential treatment of diabetes mellitus.

Delivering at least two medicaments simultaneously can create a number of concerns for a medical delivery device provider as well as for the user of the device. As just one example, the medicaments may interact with each other during the long-term storage of the formulation. Therefore, it may be advantageous to store the medicaments separately and then only combine these active components at a later point in time, such as the time of medicament administration. That is, in some arrangements, during either injection or during inhalation. However, from the standpoint of the user, combining medicaments should be patient friendly and convenient so as to result in reliable dose selection and dose injection.

A further potential concern is that the quantities and/or proportions of each medicament making up the combination therapy may need to be varied for each user or at different stages of their therapy. For example one or more medicament may require a titration period to gradually increase a patient up to a "maintenance" dose. A further example would be if one medicament requires a non-adjustable fixed dose while the other agent is varied in response to a patient's symptoms, physical condition or other patient criteria. This concern means that pre-mixed formulations of multiple active agents may not be suitable as these pre-mixed formulations would have a fixed ratio of the first and second active components, which could not be varied by the healthcare professional or patient.

Accordingly, there exists a general need to provide devices and methods for the joint delivery of two or more medicaments. According to at least one embodiment, the present apparatus and method overcomes the above-mentioned concerns by providing a solution to the above-described problems by providing an improved cannula assembly and associated injection device having a cannula that has a reservoir containing an active medication. This cannula is part of a cannula assembly that is attached to an injection device, such as a pen injection device containing a cartridge. These and other advantages will become evident from the following more detailed description of the invention. The general problem to be solved by the present invention is to provide a needle assembly where an administration of at least two medicaments is facilitated.

SUMMARY

A cannula assembly or needle assembly is described which may be used with an injection device, the assembly comprising a hub having means for attachment of the hub to an injection device. A first cannula through which a medicament may be delivered is mounted to said hub, said first cannula having a distal end and a proximal end. Furthermore, an inner space is provided in which a drug carrier is arranged. The drug carrier comprises a plurality of cavities. A first medicament is contained in the cavities. The assembly is adapted such that the first medicament may be delivered through the first cannula.

The term "mounted to" may include a direct connection or an operative connection.

The cavities of the drug carrier may be separated from each other or, as an alternative, be interconnected with each other.

The drug carrier may contain a first medicament which may be present in fluid form as well as in dry form. In case of a fluid medicament, it is preferred to choose the size of the cavities such that capillary forces keep the medicament in place unless it is rinsed out by the operation of a drug delivery device pressing a fluid through the first cannula.

The drug carrier may comprise at least one of an open pore solid foam and a fibrous material. The fibrous material may comprise hollow fiber strands. The pores of the foam and the tubes of the fibers hereby form the cavities, respectively.

According to one embodiment, the needle assembly comprises only one cannula and the first cannula itself defines the inner space in which the drug carrier is arranged.

According to another embodiment, the needle assembly comprises a housing, the housing being coupled to the hub. The housing may comprise a unitary housing. In this embodiment, the second cannula comprises a piercing proximal end which may be configured for fluid engagement with a liquid provided in the injection device and a distal end configured for fluid engagement with an inner space provided in the housing. Furthermore a first cannula is provided, comprising a proximal end configured for fluid engagement with the inner space and a piercing distal end. The drug carrier is arranged in the inner space provided by the housing. The drug carrier may comprise an active ingredient.

In general, the drug carrier may be contained in an inner cavity of the needle arrangement, the inner cavity being in fluid communication with the cannulae of the needle arrangement.

In one embodiment, the medicament may be provided in the inner space of the arrangement in the form of a dry, solid or liquid formulation.

The injection device may comprise a pen type injection device. The pen type injection device may comprise a resettable pen type injection device. The cannula assembly may be removably or permanently coupled to the injection device. Furthermore, the assembly may comprise a cover cap adapted to surround said hub and said cannula, said cover cap comprising a first open side wherein a user removable barrier is provided for sealing said first open side of said cover cap.

Furthermore, the assembly may comprise a cover cap adapted to surround said hub and at least one of said cannulas, said cover cap comprising a first open side wherein a user removable barrier is provided for sealing said first open side of said cover cap. Said cover and said user removable barrier may provide a sterile enclosure for said cannula assembly.

Furthermore, a drug delivery system is described, the system comprising the assembly as described above, and further an injection device, wherein said proximal end of said cannula of the assembly is in liquid engagement with a second medicament contained in a cartridge provided in the injection device which is configured to be coupled to the hub. By operating the injection device the second medicament is dispensed from said second medicament container through the drug carrier exiting the drug delivery system through said first cannula, thereby rinsing out said first medicament.

Said injection system may be used to administer a variable dose of said second medicament contained in said cartridge provided in said injection device for the purpose of testing the drug delivery device.

These as well as other advantages of various aspects of the presently described arrangements will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
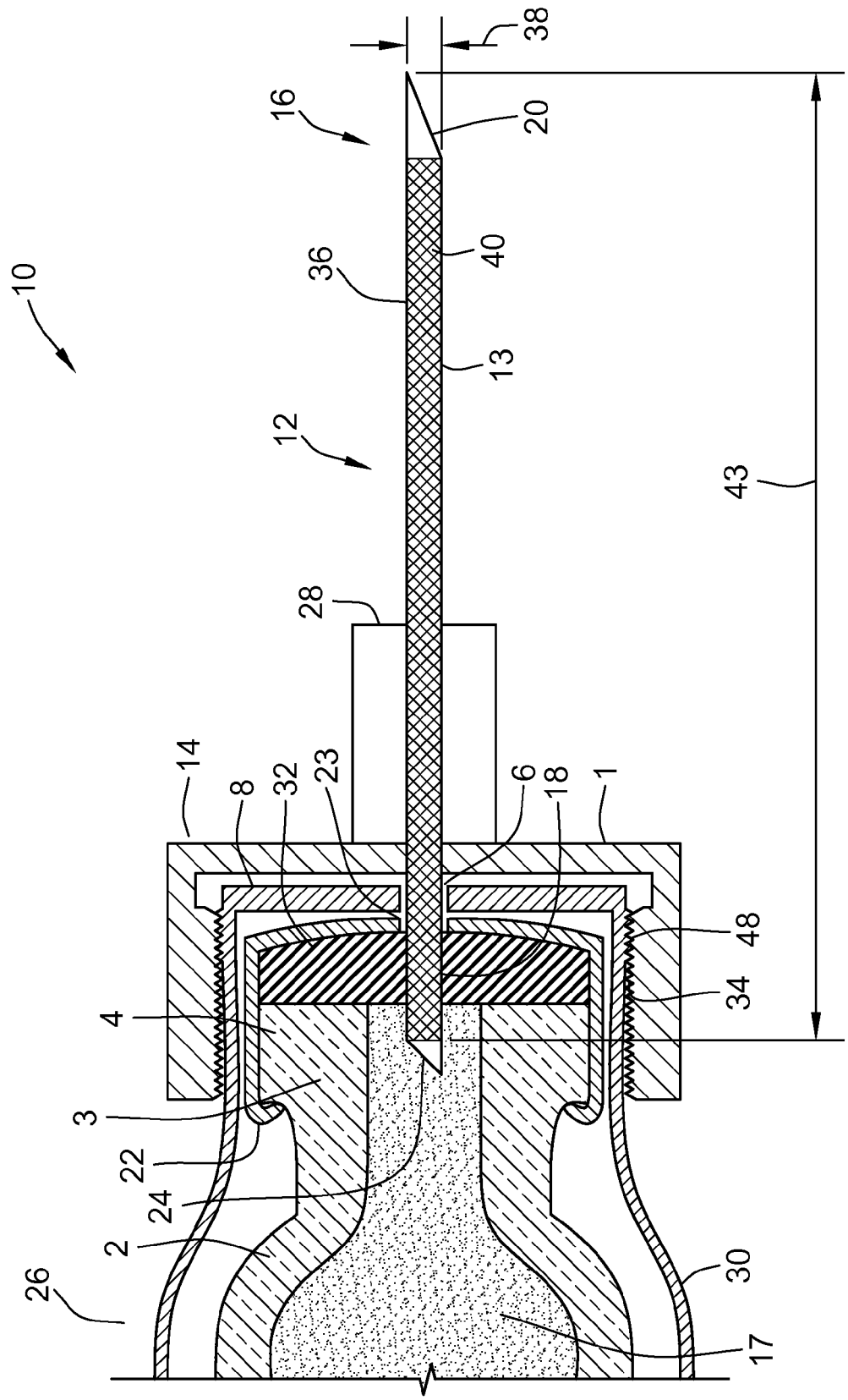
FIG. 1 illustrates a first arrangement of a cannula assembly.

FIG. 1 illustrates a first arrangement of a cannula assembly 10 containing a first medicament 40 (e.g., a medicament comprising GLP-1 or a GLP-1 analog). Such cannula assembly 10 is configured as being coupled to an injection device 26, such as the injection device illustrated in FIG. 4. In FIG. 1, a housing portion 1 of the injection device 26 is illustrated and this housing portion 1 comprises an end wall 8. This end wall 8 comprises an aperture 6. The housing portion 1 includes an outer wall 30 that surrounds and houses a cartridge or ampoule 2. Preferably, this cartridge 2 is made of glass or plastic.

The cartridge 2 contains a second medicament 17 (e.g., a medicament comprising insulin). The cartridge 2 at a distal end comprises a neck 3 defined in part by a large diameter annular bead 4. A metallic sleeve 22 is crimped around the large diameter annular bead 4 at the distal end of the cartridge 2. The metallic sleeve 22 defines a bore 23 and this sleeve 22 permanently holds a reseal-able rubber membrane 32 in place. When the cannula assembly 10 is connected or coupled to the injection device 26, a proximal end 18 of the first cannula 12 pierces this membrane 32 by moving axially within an aperture 6 of the housing 1 and within the bore 23 of the metallic sleeve 22.

The cannula assembly 10 comprises a first cannula 12 mounted in a cannula hub 14. Although FIG. 1 only illustrates a single first cannula 12 mounted in the hub 14, such an arrangement could comprise two or more cannulae.

The first cannula 12 has a distal end 16 and a proximal end 18 and both ends 16, 18 are sharpened and beveled. More specifically, the sharpened and beveled portion of distal end 16 of the first cannula 12 is designated by location 20 and the sharpened and beveled of the proximal end 18 of the first cannula 12 is designated by location 24.

The first cannula 12 is fixedly mounted in the hub 14 by way of a cannula holder 28. This cannula holder 28 may be of unitary design with the cannula hub 14. Alternatively, this cannula holder 28 may be a separate component part from the cannula hub 14. As a separate component, this cannula holder 28 helps to retain the first cannula 12 in the cannula hub 14.

In this first cannula assembly arrangement 10, the cannula hub 14 has one or more inner threaded connectors 34. These threaded connectors 34, schematically illustrated in FIG. 1, allow the cannula assembly 10 to be removably attached to a distal end of an injection device, such as the injection device illustrated in FIG. 4. Preferably, the one or more inner threaded connectors 34 may be releasably coupled to outwardly disposed threads or grooves 48 provided along an external surface of the distal end 1 of the injection device 26.

Alternative connector arrangements may also be used to releasably couple the cannula assembly 10 to the injection device 26. In such arrangements, this connector arrangement can be any connector design known to the art, preferably one that is releasable by a user. For example, such a releasable connector could comprise a single or multiple start thread, a bayonet lock, a luer lock, ramps and detents, snap locks, snap fits or other connector that has a male or female part that connects to the corresponding female or male part on the medicament housing.

FIG. 1 illustrates the cannula assembly 10 mounted on the distal portion of the delivery device. As the cannula assembly 10 is mounted on the distal end of the injection device 1, the proximal end 18 of the cannula passes through the aperture 6 of the distal end of the injection device 1 so that the sharpened and beveled end 24 pierces the membrane 32. Once the beveled end 24 pierces the membrane 32 and is then moved further in the proximal direction, the proximal end will be in fluid engagement with the second medicament 17 contained in the cartridge 2.

In an alternative arrangement, such as when the cannula assembly 10 may be used with a single dose pre-filled injection device arrangement, the hub 14 may comprise a permanent connector. In this manner, the hub 14 may be permanently attached to a medicament housing of the injection device. In such an arrangement, once an injection is complete, the entire dosing system including the injection device and the cannula assembly is disposed.

The cannula assembly 10 has a cannula inner wall 13 having a length L 43 and an inner diameter D 38. These dimensional characteristics of the cannula 12 define an inner space or reservoir 36 of the first cannula 12. As will be described in detail below, this inner space 36 allows for the first cannula to house or store a fixed amount of the first medicament 40 that may be defined as a fixed dose. Preferably, a drug carrier is arranged in the inner space 36, wherein the drug carrier comprises a plurality of cavities separated from each other, and wherein the first medicament 40 is contained in the cavities of the drug carrier.

In this manner, the cannula assembly 10 can be used to administer a combination product during a single injection of the injection device 26. Such combination product would comprise a first dose (e.g., a fixed dose contained within the inner space 36 of the first cannula 12) and a second dose. Such second dose could comprise a variable dose of the second medicament 17 stored in the cartridge 2 and selected by the injection device 26. As illustrated in FIG. 1, the first medicament 40 is shown as being deposited along the entire length L 43 of the inner wall 13 of first cannula 12. However, the medicament 40 may be provided or deposited along only a portion of this inner wall 13.

Figure 4:
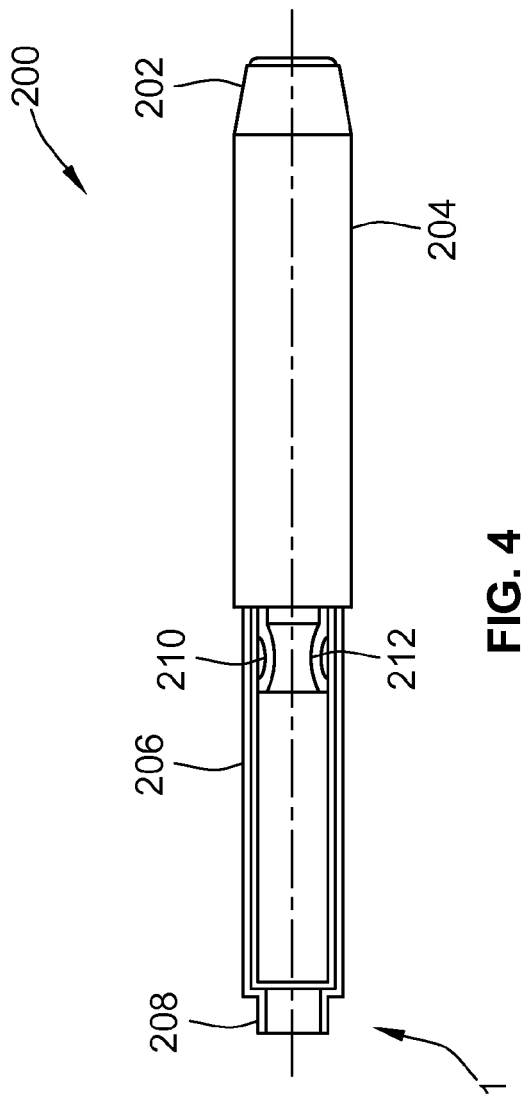
FIG. 4 illustrates an injection device for use with the cannula assembly illustrated in FIGS. 3 and 4.

With certain presently known injection devices, such as the injection device illustrated in FIG. 4, ensuring a dose of two medicaments presents certain challenges as described above. The disclosed cannula assembly provides making a certain fixed dose available in a reservoir or an inner space of the cannula assembly that contains a first medicament 40 within a cannula that is connected onto an injection device, such as a pen injection device. This pen device may then be used to set a variably dose of a medication contained within the pen device, for example the second medicament 17 contained within a cartridge or ampoule. The device can then be used to administer this variably set dose along with the active ingredient stored within the cannula assembly reservoir.

As just one example, the inner space or reservoir 36 of the cannula assembly 10 may be used to administer a fixed dose of a GLP-1 or GLP-1 analog or a combination thereof with long acting insulin, such as active ingredient 11 stored in cartridge 2. Such a long acting insulin could comprise a once a day insulin, e.g. insuline glargine. In one arrangement, a fixed dose of the GLP-1 or GLP-1 analog comprises approximately 20 µg and is provided in the inner cavity 36 defined by the cannula 12 along with a variable dose of long acting insulin contained as the second medicament 17 within the cartridge of the injection device. Such a variable dose could comprise a user settable dose of approximately from about 5 to approximately 100 units of insulin. One unit is the biological equivalent of about 45.5 microgram pure crystalline insulin.

In one preferred arrangement, the reservoir 36 containing the first medicament 40 comprises a dimension so as to accept a dose of approximately 20 µg of active pharmaceutical ingredient (API). For such a size of the API, the inner space 36 of the first cannula 12 may be used as a medicament reservoir. Alternatively, and as explained with respect to FIG. 2, this first medicament 40 may be housed in a suitable shaped cannula assembly housing. Such suitable shaped cannula assembly housing may be a single or multiple component assembly housing.

As just one example, in FIG. 1, an inner space or cavity 36 of a conventional pen type 30 Gauge (G) cannula assembly for insulin has a total length "L" 43 of approximately 23 mm. The inner diameter "D" 38 of such a 30 G cannula pen type needle assembly would be approximately 0.16 mm. Therefore, the computed volume of such a 30 G cannula inner space would be approximately $V=(Pi)*(L)*(D/2)^2$ needle pen type cannula assembly. This equates to defining a cannula reservoir or inner cavity that can hold approximately 0.46 µl of fluid. Therefore, where the cannula 12 illustrated in FIG. 1 comprises such a conventional 30 G cannula, the inner space 36 of such cannula could accept or store a dose of an active medicament 40 of approximately 20 µg of API, such as GLP-1 or a GLP-1 analog.

This approximately 20 µg of an API may take the form of an approximately 4.3% solution of API. This liquid formulation of the active pharmaceutical ingredient may contain further excipients that prevent drying-out or the cannula reservoir during storage. Suitable excipients for this purpose are e.g. glycerol, polyols, macrogols or mono-, di-, oligo- or polysaccharides. Additional closures such as needle caps on both ends of the cannula assembly and the outer packaging may further improve storage stability. Alternatively, to circumvent limited stability due to drying-out of the drug reservoir, a drying step can be intentionally performed to transfer the liquid fill of the cannula into a dry product. Suitable processes for drying are e.g. air-drying, vacuum-drying, or freeze-drying. This could lead to the manufacture of an active ingredient reservoir containing a solid drug. In such an arrangement, this solid drug may then be dissolved by using variable set dose of medication from the injection device and then this combination product could be injected. Dissolving the solid drug may be accomplished by using excipients like polyols (mannitol, xylitol), mono-, di-, oligo-, or polysaccharides (e.g glucose, fructose, saccharose, dextrates, dextrane 40) or other similar adjuvants which are known to those skilled in the art from freeze drying. These excipients maintain an amorphous state of the drug substance and prevent crystallization.

During the injection of the variable dose (that is, the dose that is set from the second medicament 17 contained in the cartridge 2 of the connected injection device 26) with the cannula assembly 10 illustrated in FIG. 1, the first medicament 40 housed in the cannula assembly reservoir is flushed. Therefore, both the first and the second medicaments 40, 17 are applied jointly to the injection site of the patient.

Figure 2:
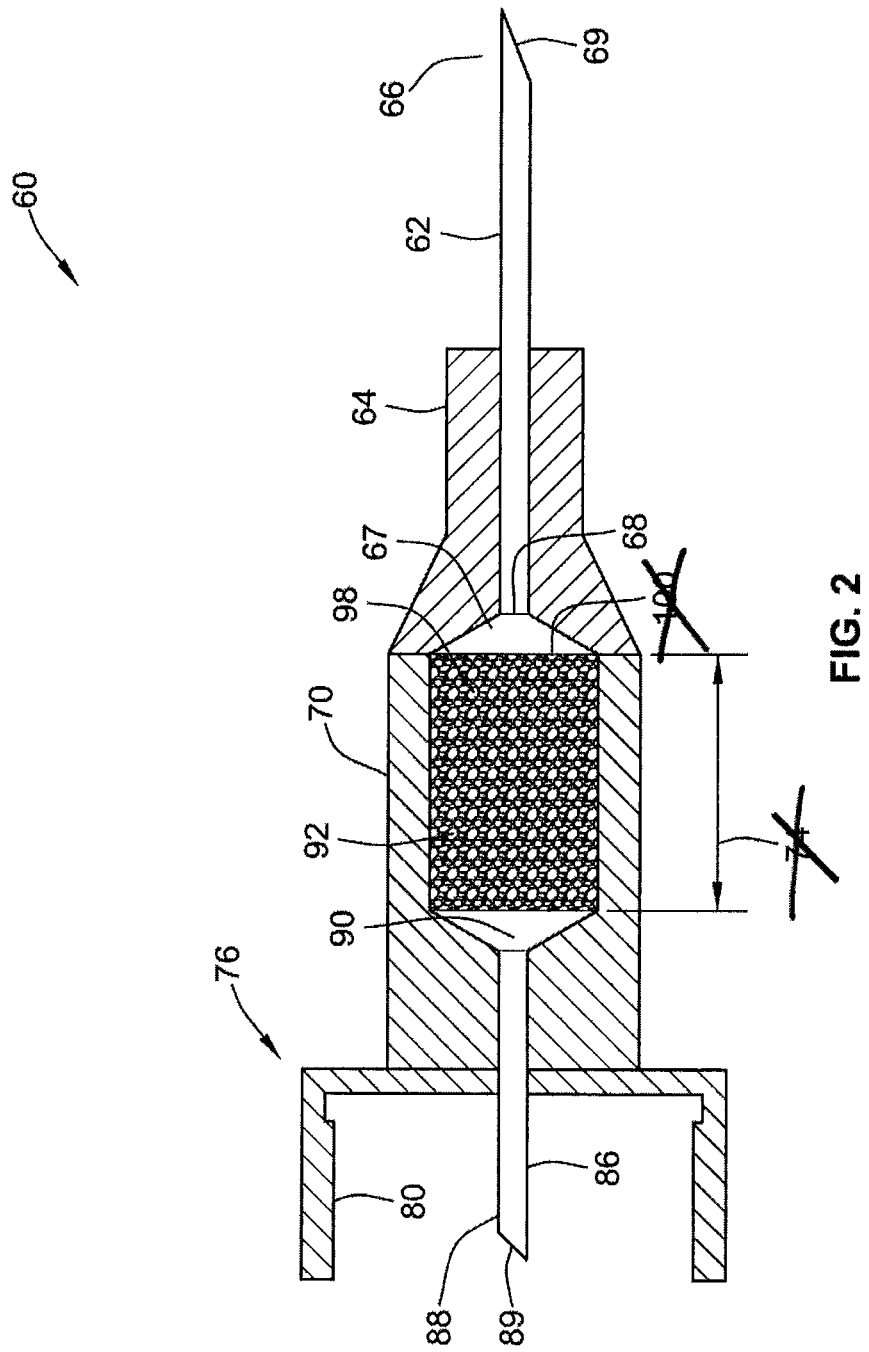
FIG. 2 illustrates a second arrangement of a cannula assembly.

FIG. 2 illustrates a second arrangement of the disclosed cannula assembly 60 that may be used with an injection device, such as the injection device of FIG. 4. In other words, as illustrated in FIG. 1, the second arrangement 60 of FIG. 2 may be coupled to the housing portion 1 and the cartridge 2 illustrated in FIG. 1.

In this second arrangement of the disclosed cannula assembly 60, the cannula assembly 60 comprises a first cannula member 62, a second cannula member 86, a cannula hub 76, a first active ingredient housing portion 70 and a second active ingredient housing portion 64. An active ingredient carrier is contained within an inner space 67 defined in part by both the first and the second active ingredient housing portions 64, 70, respectively.

In this alternative needle assembly arrangement 60, the second cannula member 86 comprises a distal end 90 and a proximal end 88. Preferably, the proximal end 88 of the first cannula member 86 is used to pierce a membrane of a cartridge or ampoule contained in the injection device, such as the membrane 32 of the cartridge 2 illustrated in FIG. 1. The proximal end 88 of the second cannula member 86 is therefore in fluid engagement with the fluid or medication contained in the cartridge. Similar to the first cannula 12 illustrated in FIG. 1, the proximal end comprises a piercing proximal portion 89 that is beveled and shaped for piercing. Preferably, the inner space of the second cannula member 86 that is in connection with the cartridge 2 contains no drug and thus can not contaminate the contents of cartridge 2.

The distal end 90 of the second cannula member 86 extends through the cannula hub 76 and the first housing member 70. This second cannula member 86 is held in place by both the hub 76 and the first active ingredient housing member 70. The distal end 90 is in fluid engagement with an inner cavity 67. This inner cavity 67 contains a drug carrier 98. In one preferred arrangement, the inner cavity 67 contains a drug carrier 98 comprising a plurality of hollow fiber strands containing a first medicament 92. Such first medicament 92 could comprise a GLP-1 or GLP-1 analog as a pure drug substance or as a either dry, solid or liquid drug formulation. In case of a liquid drug formulation, the liquid is fixed by capillary action within the inner cavities of the hollow fiber strands. In case of a dry drug substance or dry drug formulation, the drug is dispensed in liquid form onto the drug carrier 98 within the inner cavity 67, followed by a drying process such as air-drying, vacuum-drying or freeze-drying. The drying process may be accelerated through addition of volatile solvents like ethanol to the aqueous formulation dispensed. In this embodiment, the drug is trapped within the hollow-fiber cavities and fixed during storage and transport.

Coupled to the first housing member 70 is a second housing member 64. This second housing member 64 may be used to mount a first cannula member 62. This second member comprises a proximal end 68 and a distal end 66. The proximal end 68 is in fluid engagement with the drug carrier 98. The distal end 66 comprises a piercing portion 69 that may be used to pierce the skin of a user so as to provide an injection of both the first medicament contained in the cavity and the second medicament contained in a cartridge contained in the attached injection device.

As just one example, at a concentration of active ingredient of 0.1% of a GLP-1 or a GLP-1 analog, approximately 20 μg of API may be contained in a volume of 20 μl. The reservoir or inner cavity 67, which may comprise a cylindrical reservoir, may be used having dimensions of L=3 mm and H=3 mm. Such dimensions correspond to an inner cavity having a volume that can sufficiently contain 20 μl of API and can be integrated into the design of the cannula assembly 60.

For the fixation of a liquid first medicament 92 in the reservoir, an drug carrier 98 can be introduced which is dosed so as to contain a solution of the medicament. As just one example, hollow fibers, open pore foams or fibrous materials can bring about a fixation as a result of the well known effect of capillary action. Therefore, the first medicament 92 can be fixed in a fluid formulation within the inner cavity 67 defined by the first and the second active ingredient housing portions 70 and 64, respectively. Such a drug carrier material could also comprise, for example, hollow fiber strands (e.g., glass fiber, polyurethane, polyester, PTFE, polyethylene, polypropylene, poly-lactid-glycolic-acid (PLGA), etc.), open pore foams (e.g., made of polyurethane, polyvinylalcohol, polyvinylacetate), filter membrane materials (e.g., made of PTFE, PVDF, celluloseacetate, polyethersulfone, polyamide, etc.) sintered plastic beads (e.g., made of polyolefins like polyethylene, polypropylene, PTFE, PVDF, etc), fiber materials (e.g., fiber pads made of paper, plastic fiber, cellulose and cellulose derivatives, etc.).

Suitable fluid formulations contain, if necessary, additions for binding water to prevent drying out of the active ingredient during storage. For example, such suitable fluid formulations could include glycerol or macrogol or other similar type excipients. Moreover, the formulation can be transformed into a dry form for possible improvement of storage stability by way of a subsequent drying process or processes. The dissolution of the first medicament in solid form can, if required, take place in the course of a priming step with the second medicament that is contained in a cartridge or ampoule of the injection device.

The suitable carrier materials can be impregnated with the first medicament (such as GLP-1 or an analog thereof) solution in commercial processes during manufacturing prior to being mounted in a cannula housing, and afterwards be stamped into form and automatically mounted onto the needle housing. The procedures for manufacturing layer materials that contain active ingredient are, inter alia, known from topical band-aid preparations and bandage materials.

Techniques for inserting membranes into injection-molded plastic housing are, for example, known from the manufacture of syringe pre-filters. Alternatively, the first medicament can be added as solution onto the carrier material after it is mounted in a cannula housing.

Utilizing hollow fibers as the drug carrier material in the reservoir results in certain advantages. For example, hollow fibers can, if necessary, be a particularly advantageous version of the reservoir, as the hollow fiber strand can ensure a linear flow through the reservoir. In one arrangement, such hollow fibers having an inner diameter of approximately 0.1 to 0.3 millimeters (mm) can be bundled into strands of approximately 0.5 to about 5 mm diameter and a length of approximately 5 to about 20 mm and can accept the required volume of solution containing a first active ingredient.

Alternatively, rather than using hollow fiber strands as the drug carrier, open pore solid foams and fibrous materials may be used. Open pore solid foams consist of a solid structure of interconnected lamellae that form the skeleton of the foam. Void spaces of the foam are also interconnected and form a coherent structure that could be filled by a fluid. In case of fibrous materials, fibres form the solid part of the structure and between fibres void spaces are present that can take up fluid. Further, fluid can be taken up to some extent by the fibre materials itself leading to swelling. Such open pore solid foams and fibrous materials are known from the manufacture of sterile filters and depth filters. The void space of an open pore foams or a fibrous materials can be controlled by the manufacturing process of the materials and may have a defined cavity volume of approximately 50% to >95% relative to the total volume. For example, in one arrangement, where dissolving approximately 20 μg of an active ingredient such as GLP-1 or a GLP-1 analog into a solution of approximately 10 μl, approximately 20 μl of matrix volume is required if the matrix has an open pore volume of about 50%. This matrix volume can be accomplished by a cannula assembly housing, such as the assembly housing in FIG. 2, having a 2-3 mm diameter and 3-6 mm length.

Figure 3:
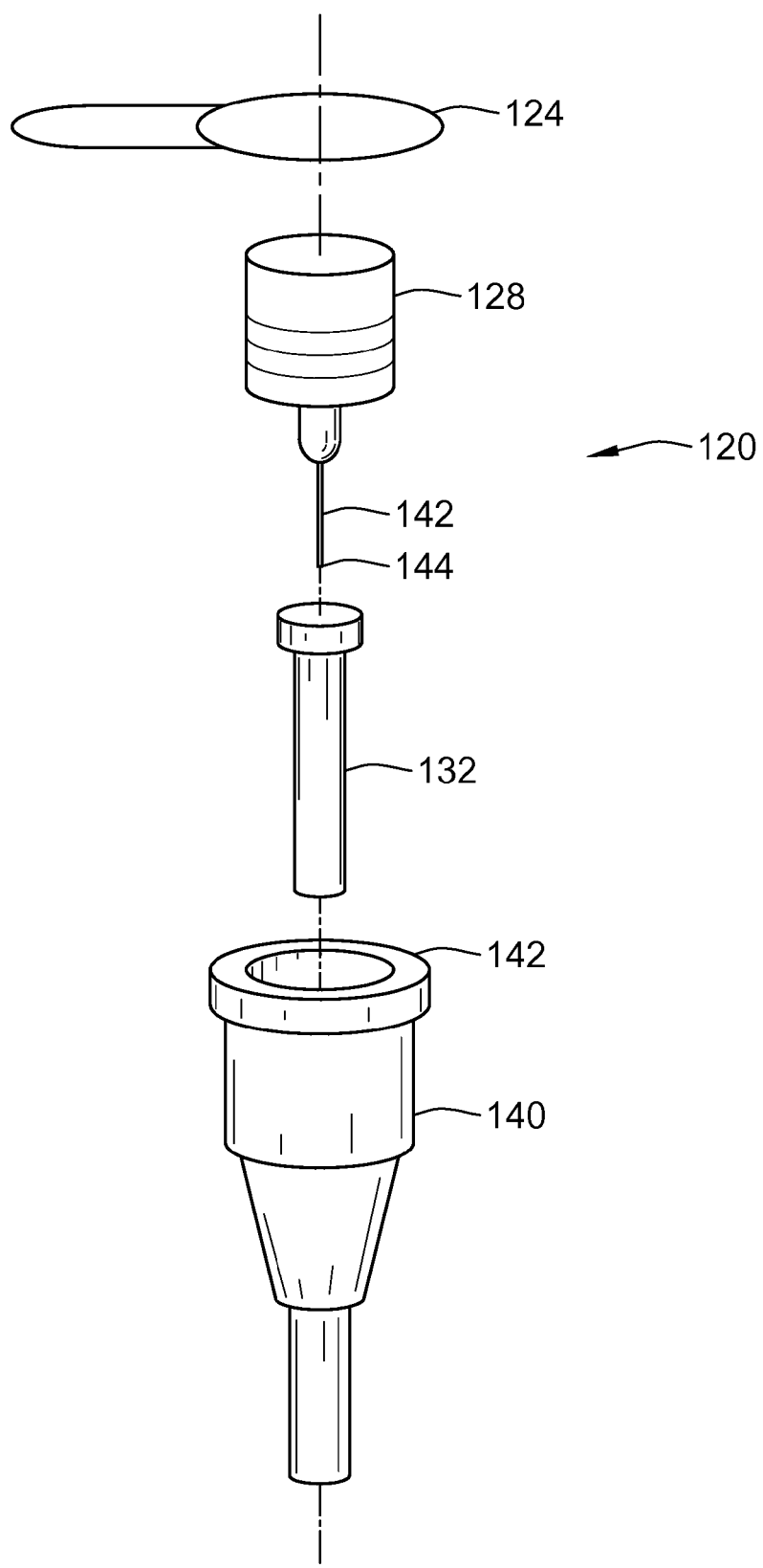
FIG. 3 illustrates a first packaging arrangement for a cannula assembly, such as the cannula assemblies illustrated in FIGS. 1 and 2.

FIG. 3 illustrates a packaging arrangement 120 for the disclosed cannula assembly, such as the cannula assembly 10 illustrated in FIG. 1 or the cannula assembly 60 illustrated in FIG. 2. This packaging arrangement 120 comprises a cover cap 140. This cover cap 140 may be used by the user to mount the cannula assembly on the injection device. For transportation and storage, this cover cap 140 along with the protective film 124 provides a sterile enclosure of the needle arrangement 128. The cover 140 is slid over the needle arrangement 128 and essentially covers the entire needle assembly 128. Before the needle arrangement 128 is slid into the cover 140, however, a needle cap 132 is provided over a distal end 144 of the cannula 142 of the assembly 128 so as to prevent, in part, an inadvertent needle stick. As may be seen in FIG. 3, a protective film 124 is also provided. This protective film 124 covers an opening 142 of the cover 140 so as to provide a completely sealed, sterile enclosure. This protective film 124 may be welded or adhesively bonded to the opening 142 of the cover 140.

Before a user mounts the cannula assembly to an injection device, this protective film 124 is torn off by the user. Then the cover cap 140 may be used to mount the cannula assembly 128 onto the injection device. Once mounted, the cover and the needle shield 132 may be removed so as to allow injection. After use, the cover 140 can be slid back over the cannula assembly 128 and may be used to remove the needle assembly from the connected injection device. In order to prevent a possible accidental needle stick, the needle cover 132 may be used to cover the distal end of the cannula 142 before the needle assembly is removed from the injection device.

Figure 5:
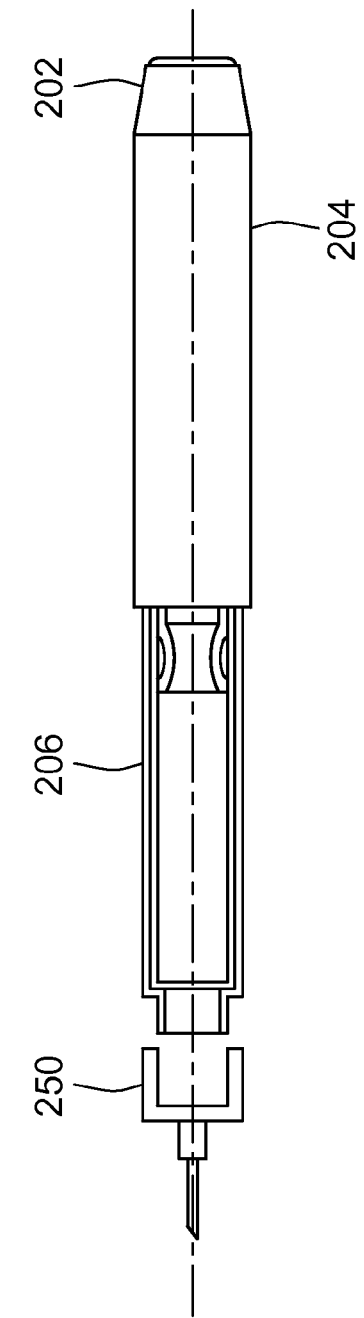
FIG. 5 illustrates one arrangement of a cannula assembly mounted on the injection device illustrated in FIG. 4.

The disclosed cannula assembly is designed to operate in conjunction with a multiple use injection device, preferably a pen-type multi-dose injection device, similar to what is illustrated in FIG. 1. Such an exemplary injection device 200 is illustrated in FIG. 4. FIG. 5 illustrates one arrangement of the disclosed cannula assembly 250, similar to the cannula assembly 10 illustrated in FIG. 1, mounted to such a conventional drug delivery device 200. The first medicament (40, 92) is kept in place within said cannula assembly (10, 60) unless it is rinsed out by the operation of a drug delivery device pressing a fluid, e.g. the second medicament 17, through said drug carrier 98 and through the first cannula (12, 62).

The injection device 200 could be a reusable or disposable device. By disposable device it is meant an injection device that is obtained from the manufacturer preloaded with medicament and cannot be reloaded with new medicament after the initial medicament is exhausted. The device may be a fixed dose or a settable dose, but in either case it is a multi-dose device.

In FIG. 4, the conventional device 200 comprises a cartridge housing 206, a dose dialing module 204, and a dose adjustment knob 202. A first end of the cartridge housing 206 and the dose dialing module 204 are secured together by retaining features. Such typical injection device 200 contains a cartridge or other reservoir of medication. This cartridge is typically cylindrical in shape and is usually manufactured in glass. The cartridge is sealed at one end with a rubber bung and at the other end by a rubber septum. The injection pen is designed to deliver multiple injections. It therefore has features, for example a screw thread, which are used to attach an injection cannula assembly, such as the cannula assembly illustrated in FIG. 1. As discussed with reference to FIGS. 1 and 2, the disclosed cannula assembly is designed to pierce the cartridge septum and provide fluid communication between the contents of the cartridge and the subcutaneous region of the patient.

The medicament contained with the cartridge housing 206 is expelled by a mechanism in the injection device that causes the cartridge bung to advance. The delivery mechanism is typically powered by a manual action of a user; however, the injection mechanism may also be powered by other means such as a spring, compressed gas or electrical energy.

In one arrangement, the cannula assembly 250 can be designed to work with currently marketed pen-type injection devices or alternatively, the cannula assembly 250 may be designed to work with only a particularly designed injection device. This could be achieved by including specific connecting or coupling features on the injection device that engage matching or complementary features on the cannula assembly 250. For example, specific coupling or connecting features may be provided on the distal end 208 of the injection device 200 that engage matching or complementary features on a specific type of cannula assembly 250 for use with only one type of injection device. As just one example, a specific type of cannula assembly 250 containing a fast acting insulin as an active ingredient, such as insuline glulisine, may only be allowed to be connected to only a specific type of injection device containing a long acting insulin, such as insulin glargine. However, those of skill in the relevant art will recognize alternative mechanical arrangements and active ingredient arrangements are also possible. One reason for restricting the use of the injection system to a particular cannula assembly is to ensure dose accuracy of the medicament delivered from the injection device. Another reason for restricting the use of the injection system to a particular cannula assembly is to ensure that only certain active medicaments can be delivered along with only certain other active medicaments stored within the injection device.

There are a number of advantages to the presently disclosed cannula assembly. For example, one advantage is that exact dosing of low-dose active ingredients may be achieved. Dosing is ensured by the single dose and is not dependent on tolerances of the dosing system (device) or variability of multi-dose packaging, e.g. a cartridge/stopper system.

In addition, the presently claimed cannula assemblies allows for the combination of a fixed dose with a variable dose. In other words, a fixed dose can be combined with a large range of variable doses. Limitations may arise with respect to a minimum quantity of the variable dose which is required for flushing the active ingredient out of the reservoir. Other technical solutions, such as, for example, devices with several cartridges for fixed and variable doses are extremely expensive to create and perhaps complicated to handle.

Moreover, the disclosed cannula assembly results in a simple and safe to user application. In other words, by simply mounting of the cannula system with an active ingredient reservoir onto an injection device, operation is scarcely different from known device systems and is conceivably easy. One potential result is that higher safety of use can be achieved.

As yet another advantage, the disclosed cannula assembly results in a cost-effective, commercial manufacture of individual doses. That is, by using automated systems, commercial and cost-effective manufacture of individual doses can be attained, whereby known manufacturing principles can be resorted to.

Exemplary embodiments of the present invention have been described. However, changes and modifications may be made to these embodiments without departing from the true scope and spirit of the present invention, which is defined by the claims.

Reference Numerals
1 housing portion
2 cartridge/ampoule
3 neck
4 diameter annular bead
6 aperture
8 end wall
10 cannula assembly
17 second medicament
12 first cannula
13 wall
14 cannula hub
16 distal end
18 proximal end
20 location
22 metallic sleeve
23 bore
24 location
26 injection device
28 cannula holder
30 outer wall
32 rubber membrane
34 inner threaded connectors
36 inner space/reservoir
40 first medicament
48 threads/grooves
60 cannula assembly
62 first cannula member
64 second active ingredient housing portion
66 distal end of the first member
67 inner space
68 proximal end of the first member
69 piercing portion
70 first active ingredient housing portion
76 cannula hub
86 second cannula member
88 proximal end
89 proximal portion
90 distal end
92 first medicament
98 drug carrier
120 packaging arrangement
124 protective film
128 needle arrangement
132 needle cap
140 cover cap
142 cannula
144 distal end
200 injection device
202 dose adjustment knob
204 dose dialing module
206 cartridge housing
208 distal end
250 cannula assembly

The invention claimed is:

1. A needle assembly attachable to an injection device comprising a cartridge, the needle assembly comprising:
   i) a hub attachable to the injection device,
   ii) a cannula mounted to said hub, said cannula having a distal end, and a proximal end, wherein the distal end and the proximal end of the cannula comprise beveled portions, and
   iii) an inner space, in which a drug carrier is arranged, wherein the drug carrier comprises a plurality of cavities, and
   wherein a first medicament is contained in the cavities,
   wherein the proximal end of the cannula is configured for fluid engagement with a fluid or medication contained in the cartridge of an injection device; and
   wherein the assembly is adapted such that the first medicament can be delivered through the cannula, and
   wherein the inner space is arranged between the distal end and the proximal end of the cannula.

2. The needle assembly of claim 1 wherein said medicament is selected from the group comprising an active pharmaceutical ingredient; a formulation of an active pharmaceutical ingredient; a dry, solid formulation; or a liquid formulation.

3. The needle assembly of claim 2 wherein said dry solid formulation is selected from the group comprising excipients to facilitate rapid dissolution of said formulation; excipients to facilitate rapid dissolution of said formulation, the excipients selected from the group comprising mono-, di-, oligo-, or polysaccharides, dextran or polyols.

4. The needle assembly of claim 1 wherein a formulation comprises a liquid formulation, said liquid formulation selected from the group comprising excipients to prevent drying-out of said formulation; or excipients to prevent drying-out of said formulation, the excipients selected from the group comprising glycerol, polyols, macrogol or mono-,di-, oligo- or polysaccharides.

5. The needle assembly of claim 1 wherein said drug carrier comprises at least one of an open pore solid foam and a fibrous material.

6. The needle assembly of claim 5 wherein said fibrous material comprises hollow fiber strands.

7. The needle assembly of claim 1 wherein said first medicament defines a fixed dose of an active pharmaceutical ingredient.

8. The needle assembly of claim 1 wherein said first medicament comprises 1 to 50 μg of an active pharmaceutical ingredient.

9. The needle assembly of claim 1 wherein said first medicament comprises GLP-1 or a GLP-1 analog.

10. The needle assembly of claim 1 wherein the needle assembly is configured such that said first medicament can be rinsed out by a fluid pressed through said drug carrier and said first cannula.

11. A drug delivery system comprising the assembly of claim 1, and further an injection device, wherein said proximal end of said cannula is in liquid engagement with a second medicament contained in a cartridge provided in the injection device.

12. A drug delivery system of claim 11 wherein the drug delivery device is configured such that said first medicament is rinsed out by pressing the second medicament through said drug carrier and said cannula when said drug delivery device is operated.

13. The system of claim 11 wherein said second medicament comprises a type of insulin.

* * * * *